United States Patent [19]
Oshlack et al.

[11] Patent Number: 5,324,351
[45] Date of Patent: Jun. 28, 1994

[54] AQUEOUS DISPERSIONS OF ZEIN AND PREPARATION THEREOF

[75] Inventors: Benjamin Oshlack, New York, N.Y.; Mark Chasin, Manalapan, N.J.; James McGinity; Roland Bodmeier, both of Austin, Tex.

[73] Assignee: Euroceltique, Luxembourg, Luxembourg

[21] Appl. No.: 930,107

[22] Filed: Aug. 13, 1992

[51] Int. Cl.$^5$ ............................................. C08L 89/00
[52] U.S. Cl. ....................................... 106/153; 530/373
[58] Field of Search ........................... 106/153; 530/373

[56] References Cited

U.S. PATENT DOCUMENTS

| | | | |
|---|---|---|---|
| 2,272,488 | 2/1942 | Swallen | 106/153 |
| 2,377,237 | 5/1945 | James | 106/153 |
| 2,676,169 | 4/1954 | Baldoni | 530/373 |
| 2,791,509 | 5/1957 | Cosler | 436/302 |
| 3,365,365 | 1/1968 | Butler et al. | 514/221 |
| 3,370,054 | 2/1968 | Loew | 530/373 |
| 3,371,015 | 2/1968 | Sjogren et al. | 424/477 |
| 4,931,295 | 5/1990 | Courtright et al. | 426/5 |
| 4,983,403 | 1/1991 | Ardaillon et al. | 426/2 |

OTHER PUBLICATIONS

Swallen, "Zein," *Industrial and Engineering Chemistry*, pp. 394-398, Mar. 1941.
Marley et al., "Binary Solvents for Zein", *Industrial and Engineering Chemistry*, pp. 661-665, Jun. 1943.

*Primary Examiner*—David Brunsman
*Attorney, Agent, or Firm*—Steinberg, Raskin & Davidson

[57] ABSTRACT

Aqueous dispersions of zein which may be used in the coating of pharmaceutical, animal, health, or food products in an inorganic solvent-free environment are disclosed, as well as methods for preparing the same.

24 Claims, No Drawings

AQUEOUS DISPERSIONS OF ZEIN AND PREPARATION THEREOF

BACKGROUND OF THE INVENTION

Coatings have long been applied to pharmaceuticals, animal health products, and food products for various reasons, including masking unpleasant taste, protecting components from degradation, controlling the site of drug release (enteric coating), controlling the absorption of the drug compound by retarding release of the drug from the dosage form, improving the appearance of the product, and changing the physical surface characteristics of the ingredients.

The oldest method of coating is perhaps sugar-coating. In sugar coating, the objects to be coated are moistened with an aqueous sugar solution and tumbled (for example in a rotating pan), and then dried. The moistening and drying procedures are generally repeated many times before satisfactory protection of the object to be coated and a smooth surface are obtained.

It is generally considered desirable to apply a seal coat directly over the uncoated tablet, etc. in order to separate the object to be coated from the water that is used in the coating process. Many substances have been used as sealing agents in this step, including cellulose-acetate-phthalate, zein, shellac, and other specific resins. Thereafter, the product may be subcoated, syrup coated, finished, and polished, although many variations of these procedures are used. The sealing coat is applied as a dilute, nonaqueous solution, and not more than two or three thin coats are used to seal the tablets.

More recently, film-coating techniques that have used a wide variety of materials of coating agents have been developed, in order to overcome the host of problems that can be encountered in attempting to sugar coat a tablet, such as color spotting, cracking of the coating, degradation of the drug in the tablet, and excessive subcoatings which cause retardation of disintegration and bioavailability.

Most film-coats are prepared by depositing one or more film-forming polymers onto the object to be coated, resulting in coatings that represent usually from about 2 to 10% by weight of the coated tablet. Such film coatings tend to have better resistance to chipping of the coating, increased tablet strength, and decreased production cost as compared to sugar coating. The polymers used in film-coating are generally water soluble or water dispersible cellulose derivatives such as hydroxypropyl methylcellulose and carboxymethylcellulose.

Hydrophobic polymers such as certain cellulose derivatives, acrylic resins, waxes, higher aliphatic alcohols, and polylactic polyglycolic acids have been used in the development of controlled release pharmaceutical dosage forms, such as tablets, capsules, suppositories, spheroids, beads or microspheres by, e.g., overcoating the individual dosage units with these hydrophobic polymers.

It is known in the prior art that these hydrophobic coatings can be applied either from a solution, suspension or as dry powders. Since most of these polymers have a low solubility in water, they are usually applied by dissolving the polymer in an organic solvent and spraying the solution onto the individual drug forms (such as beads or tablets) and evaporating off the solvent.

The use of organic solvents in the preparation of polymer coatings is considered problematic as the formulations have inherent problems with regard to flammability, carcinogenicity, and safety in general. In addition, the use of organic solvents is not favored due to environmental concerns.

Most commercially available aqueous dispersions of pre-formed polymers (e.g., ethylcellulose-Aquacoat ®, Surelease ®) are prepared via emulsification of organic polymer solutions or polymer melts into an aqueous phase followed by homogenization. Organic solvents used in this process are water-immiscible.

While coatings for pharmaceutical formulations, etc., comprising zein are considered desirable, the use of such coatings has been limited because zein is not soluble in water-immiscible organic solvents and therefore cannot be prepared by the traditional emulsification techniques described above.

With regard to confectionery coatings, U.S. Pat. No. 2,791,509 (Cosler) describes a coating for non-cereal confectionery articles which comprises zein and acetylated glycerides which are applied to the food articles in an edible organic solvent vehicle, such as 90% ethanol, or ethanol denatured with a minor amount of ethyl acetate. However, it is stated therein that virtually any organic solvent can be used which is edible, nontoxic, and in which the zein and acetylated monoglyceride are soluble. The coating is said to form a continuous barrier against the penetration of water into the confectionery and against penetration of fat, oil and moisture from the interior of the confectionery to the outside.

U.S. Pat. No. 4,931,295 (Courtright, et al.) is related to methods for producing a chewing gum with a zein coated "delayed release" high-potency sweetener. The term "delayed release" as used therein is intended to infer a delayed release of the high-potency sweetener during chewing of the gum and during storage. In this process, the zein is mixed with a solvent for the zein, and a water soluble modified cellulose compound such as HPMC to form a modified zein solution. This modified zein solution is applied to a high-potency sweetener and then dried to produce the delayed release sweetener particles. The particles are then added to a chewing gum formulation. In a preferred embodiment, the zein is dissolved in water having a pH of between about 11.5 and about 12.1 and contains about 13 weight percent zein. The zein is said to be either completely dissolved or a major portion of the zein is dissolved and a minor portion is suspended in the water. In a second preferred method, the zein is dissolved in ethanol, to between about 10–15% by weight of the solution. The zein is said to comprise about 1–15% of the coated high-potency sweetener, the zein, and the HPMC.

U.S. Pat. No. 3,371,015 (Sjogren, et al.) describes tablet coatings comprising an inner layer of a polyethylene glycol which is soluble in water and in certain organic solvents, and an outer layer of a film-forming thermoplastic substance which is water-insoluble but soluble in volatile organic solvents. Substances which are considered to be suitable for the outer layer include cellulose acetates, acrylic resins, silicone resins, as well as shellac and zein.

U.S. Pat. No. 3,365,365 (Butler, et al.) describes pharmaceutical compositions in the form of beadlets suitable for filling into hard shell capsules, wherein the beadlets are enteric coated with a coating containing zein and an abietic acid type rosin. The enteric coating which is used for preparing chlordiazepoxide beadlets are produced by mixing the abietic acid type rosin with zein, a wetting agent, an anhydrous lower aliphatic alcohol, and a plasticizer.

U.S. Pat. No. 3,370,054 (Loew) describes deaminated zein dispersible in solutions having a pH of at least 6.5 which is prepared by hydrolyzing zein with strong alkalies, and thereafter removing the alkali by precipitation.

U.S. Pat. No. 4,983,403 (Ardaillon, et al.) describes a biologically active substance for the feeding of ruminants. The composition consists of a ruminant feed additive coated with a mixture consisting of zein in combination with a non-water-soluble polymer; a hydrophobic substance; a non-water-soluble polymer and a plasticizing agent; or a hydrophobic substance and a non-water-soluble polymer. The coating mixture is said to be obtained by dispersing or dissolving zein in a solution or dispersion of the non-water-soluble polymer and/or of the hydrophobic substance, and optionally, the plasticizing agent, in an organic solvent or in a mixture of suitable organic solvents. The coating mixture is obtained after evaporation of the solvent or solvents.

OBJECTS AND SUMMARY OF THE INVENTION

It is therefore an object of the present invention to prepare aqueous dispersions of zein to be used in the coating of pharmaceutical, animal, health, or food products in an organic solvent-free environment.

It is a further object of the present invention to prepare a solid powder of zein in a redispersible form which thereafter may then be dispersed by the consumer prior to the coating process.

In view of the above objects and others, the present invention is related to aqueous dispersions of zein and methods for preparing the same.

More particularly, the present invention is related to an aqueous dispersion of zein, the aqueous dispersion comprising from about 0.1 to about 10 percent zein. The aqueous dispersions of the present invention preferably have a pH from about 4 to about 6. Generally, the particle size of the zein in the aqueous dispersion is from about 0.01 to about 2 μm. The aqueous dispersion is essentially free of organic solvents.

The present invention is also related to a method for preparing an aqueous dispersion of zein, wherein a solvent mixture comprising water and from about 60 to about 90 percent of an organic solvent selected from the group consisting of ethanol, acetone, and mixtures thereof is prepared, zein is added to the solvent mixture in such a proportion to the solvent mixture that the zein dissolves in the solvent mixture, and the zein is precipitated as fine particles to obtain an aqueous dispersion comprising from about 0.1 to about 10 percent w/v of zein.

In a preferred embodiment, the method further comprises the steps of pouring the solution of zein as a thin stream into an aqueous phase under continuous stirring to thereby precipitate the zein as fine particles. The organic solvent is then evaporated from the mixture, and the resulting aqueous phase is concentrated to a zein concentration from about 0.1 to about 10% w/v.

The present invention is also related to a powdered, redispersible form of zein. This zein powder may be redispersed prior to use in a coating process.

DETAILED DESCRIPTION

Zein is a protein of the prolamine class which is a fraction of a protein contained in corn. Commercially, it has been obtained, for example, by extracting corn gluten with a 60-80% isopropyl alcohol under alkaline conditions. After neutralization and concentration, the extract containing the zein is sprayed into cold water, causing the zein to precipitate. See, e.g., U.S. Pat. No. 2,676,169 (Baldoni) and the patents cited therein.

In the past, zein has found many uses as a coating material. However, the use of zein as a coating material has been considered problematic because zein does not bar the migration or transfer of moisture, and has been known to form a relatively hard coating having a low tensile strength and is easily fractured. As a coating material for food products, zein coatings are known to form relatively hard and crunchy coatings.

Zein is soluble in aqueous alcohols, glycols, and acetone/water mixtures. The preparation of zein dispersions is governed by the solubility properties of this natural polymer. Zein is not soluble in water-immiscible organic solvents (e.g., methylene chloride) which are commonly used to prepare pseudolatexes by emulsification techniques.

In accordance with preferred embodiment of the present invention, zein dispersions are prepared by dissolving zein in a mixture of water with either ethanol and/or acetone.

Preferably, in order to maximize the amount of zein in the dispersion, the solvent mixtures used in the present invention have a volume percentage of ethanol, acetone or mixtures thereof from about 60 to about 90 percent. However, it is possible to obtain an aqueous dispersion according to the present invention with a lower amount of the organic solvent.

Instead of ethanol and/or acetone, other organic solvent/water systems may be used to dissolve the zein. For example, the solvent mixtures of the present invention may comprise isopropanol, methanol, and the like. Isopropanol and/or methanol in a ratio of 7:3 (organic solvent/water) work up to a zein concentration of about 10% zein w/v. At higher percentages (e.g., 15% zein w/v) a gel is formed. Other solvent systems, such as ethyl acetate, DMF and DMSO may also work but have undesirable properties relative to the preferred embodiments wherein the organic solvent comprises ethanol/water and/or acetone/water.

It has been discovered that more than 40% w/v zein can be dissolved in solvent mixtures with a volume percentage of ethanol and/or acetone between from about 60 to about 90. The viscosity of these concentrated solutions is relatively high.

In a preferred embodiment of the invention, the solution of zein is poured onto an agitated aqueous phase. Zein precipitates as fine particles resulting in colloidal dispersions. These dispersions are then preferably concentrated, e.g., by evaporating water.

The upper limit of zein in the zein dispersions of the present invention are zein concentrations of about 10% w/v. Higher concentrations have been found to result in lump formation. After concentrating the dispersions of the present invention, it has been found that the maximum solids content obtainable is about 10% w/v. Lumping and sticking to the vessel are observed at higher solids content.

The pH of the aqueous zein dispersions of the present invention is generally in the range from about pH 3 to about 7. In preferred embodiments of the present invention, the zein concentration in the aqueous dispersion is from about 6 to about 10% w/v, and the pH is from about 4 to about 6. In most preferred embodiments, the aqueous zein dispersion has a pH from about 4.5 to about 5.5. When the pH of an aqueous zein dispersion of 6-10% w/v is adjusted substantially above pH 6 or below pH 4 via the use of electrolytes or buffers, the dispersion has been found to become unstable and a fine dispersion of zein is no longer obtained which would be suitable for commercial applications, such as in spray coatings. For example, at least a portion of the zein particles will no longer be in a desirable nanoparticle size range. The zein in the dispersion may precipitate, agglomerate, and/or flocculate at such pH levels. Stability may be achieved at substantially higher pH's, e.g. pH 9-10 or above. As indicated in the Merck Index, zein is soluble in alkaline solutions of pH 11.5 or greater. Therefore, it is possible that at pH 9-10 and above, a portion of the zein in the aqueous dispersion is solubilized.

If an adjustment of the pH of the aqueous dispersion is deemed desirable, it may be possible to do so via the use of an inorganic or organic monomeric or polymeric acidic or basic compound which do not ionize to any substantial degree without causing precipitation, agglomeration and/or flocculation in the aqueous pseudolatex dispersion.

In another embodiment of the present invention, the pH of the aqueous zein dispersion can be adjusted by adding a suitable buffer system to adjust the pH of the aqueous zein dispersion to above about pH 9. For example, suitable buffer systems include an ammonium carbonate-ammonia buffer, a citric acid-sodium phosphate buffer, and a boric acid-potassium chloride-sodium hydroxide buffer.

In a preferred embodiment, the particle size of the zein in the aqueous dispersion is from about 0.01 to about 2.0 μm, although depending upon the desired use of the end product, larger particle sizes may be acceptable. In most preferred embodiments of the present invention, the majority of the zein particles in the resultant aqueous dispersion are from about 100 to about 300 nanometers.

In another embodiment of the present invention, a zein dispersion is prepared as set forth above and then is dried to obtain fine particles, preferably smaller than about 10 μm. The fine particles of zein which are obtained are preferably in the size range from about 0.1 to about 5.0 μm. The zein dispersion may be dried by any suitable method known to those skilled in the art, such as spray drying, freeze drying, etc. The zein powder may thereafter be redispersed in an aqueous solution when so desired.

The use of a redispersible zein powder is desirable for a variety of reasons. First, microbiological concerns and the necessary addition of preservatives to the aqueous dispersion would be minimized or eliminated. Secondly, the redispersible zein powder of the present invention results in reduced shipping volumes and a greater flexibility at the formulation stage.

The aqueous dispersions of zein used as coatings in the present invention may be used in virtually any application in which a coating would be desirable, including use in conjunction with food products, animal health products, confectionery products, and various pharmaceuticals, including tablets, spheroids (or beads), microspheres, seeds, pellets, ion-exchange resin beads, and other multi-particulate systems in order to obtain a desired controlled release of the therapeutically active agent. Granules, spheroids, or pellets, etc., prepared in accordance with the present invention can be presented in a capsule or in any other suitable dosage form.

The coating formulations of the present invention should be capable of producing a strong, continuous film that is smooth and elegant, capable of supporting pigments and other coating additives, non-toxic, inert, and tack-free. To achieve this objective, other suitable pharmaceutically acceptable agents may be added to the dispersion. For example, the inclusion of a plasticizer may be desirable in the event that the film formed by the zein coating is otherwise too brittle. The addition of a surfactant may also be desirable. Water-soluble plasticizers, e.g., glycerin, propylene glycol, and PEG 400, are preferred in comparison to the water-insoluble plasticizers, e.g., dibutyl sebacate (DBS), triethyl citrate (TEC), tributyl citrate (TBC), acetyltributyl citrate (ATBC), and acetyltriethyl citrate (ATEC). Propylene glycol at a concentration from about 20 to about 25%, based on the amount of zein, appears to be the best plasticizer. Certain plasticizing agents, such as polypropylene glycol and polyethylene glycol, have been found to solubilize part of the protein (zein) as well as plasticize the film. The resultant product therefore comprises a solution of zein as well as a dispersion of zein.

In preferred embodiments, the plasticizer is water-soluble and is incorporated in a sufficient amount to provide a desired flexibility to the film to be made from the aqueous zein dispersion of the present invention. The amount of plasticizer added is preferably from about 20 to about 40 percent, based on the zein content.

One skilled in the art will recognize that the selection of such additional pharmaceutical agents and the level of inclusion of these agents in the zein latex should be optimized for the particular use. Also, in the case of pharmaceutical coatings, once the beads, tablets, etc. have been successfully coated, the dissolution properties of the particular formulation can be optimized.

DETAILED DESCRIPTION OF THE PREFERRED EMBODIMENTS

The following examples illustrate various aspects of the present invention. They are not to be construed to limit the claims in any manner whatsoever.

EXAMPLES 1-2

Determining the Solubility of Zein

The approximate solubilities of zein in different ethanol:water and acetone:water (v/v) mixtures are determined. In Example 1, dehydrated ethanol USP obtained from a commercially available source (Midwest Grain Products Co., Pekin, Ill.) is added in different proportions (0/10, 2/8, 4/6, 5/5, 6/4, 7/3, 8/2, 9/1, 10/0) to water. Next, a commercially available zein-granular powder (Freeman Industries, Inc. Tuckahoe, N.Y.) is added to 10 ml of each of the solvent mixtures in a glass vial. The mixtures are then agitated in a horizontal shaker. The solubility (w/v) is then determined. The results are set forth in Table 1 below.

Example 2 is prepared in similar fashion to Example 1, with acetone from a commercially available source (Mallinckrodt Inc., Paris Ky.) being substituted for the ethanol. The results are similar to those set forth for Example 1.

TABLE 1

| | Solubility of Zein in Ethanol/Water Mixtures | | | | | | | | |
|---|---|---|---|---|---|---|---|---|---|
| Ingredient | Amount | | | | | | | | |
| ethanol/water (v/v) | 0/10 | 2/8 | 4/6 | 5/5 | 6/4 | 7/3 | 8/2 | 9/1 | 10/0 |
| zein (g in 10 ml) | 0.20 | 0.20 | 0.20 | 1.0 | 0.40 | 4.00 | 4.00 | 4.00 | 0.20 |
| solubility (w/v) | <0.1% | <2% | <2% | ≈10% | ≈40% | ≈40% | ≈40% | ≈40% | <0.1% |

As can be seen from the results set forth in Table 1, more than 40% w/v zein can be dissolved in solvent mixtures with a volume percentage of ethanol or acetone between 60 and 90. The viscosity of these concentrated solutions is high.

EXAMPLES 3-5

Preparation of Aqueous Dispersion of Zein—Precipitation Method

In Example 3, solutions of zein in ethanol/water or acetone/water are poured as a thin stream into an aqueous phase under continuous stirring. In Example 3, the solvent mixture used is ethanol:water (8:2 v/v), whereas in Example 4 the solvent mixture used is acetone:water (8:2 v/v).

In Examples 3-4, 200 ml of the solvent mixture (ethanol/water and acetone/water, each in a ratio of 8:2 v/v, respectively) is prepared, and then 10% w/v zein is added. The resultant zein solution is poured as a thin stream into 200 ml water. The zein precipitates immediately as fine particles resulting in colloidal dispersions. Stirring is continued to evaporate the organic solvent and concentrate the aqueous phase, the alcohol and some water are evaporated off at room temperature to provide an aqueous dispersion of zein (e.g., 6-10% w/v zein, and preferably 6-8% zein).

The pH of the resulting aqueous zein dispersion is less than about 4.5. The average particle size of the zein latex obtained by the evaporative method is from about 240 nm to about 300 nm, as determined by photon correlation spectroscopy (BI-200SM goniometer, BI-2030 digital correlator, Melles Griot 10 mW He-Ne laser, Brookhaven Instruments Corporation, Holtsville, NY). Latexes are formed at zein concentrations of 6% w/v and 3% w/v.

In Example 5, zein dispersions are prepared by dissolving zein in ethanol/water (6/4, v/v). The resulting solution is poured onto an agitated aqueous phase. Zein precipitates as fine particles resulting in colloidal dispersions. These dispersions are then concentrated.

Further investigations considered formulation variables such as the zein concentration, the volume of the zein solution, the volume of the external aqueous phase, and the addition of surfactants. From the results obtained, it was determined that the upper limit of zein concentration in the aqueous zein dispersions is about 10% w/v; higher concentrations of zein result in lump formation. Moreover, after concentrating the dispersions, the maximum solids content obtainable by this method is about 8% w/v. The addition of sodium lauryl sulfate caused immediate flocculation of the dispersion, possibly due to the opposite charges present.

EXAMPLES 6-7

Preparation of Aqueous Dispersion of Zein—Evaporation Method

In Example 6, zein is added to solvent mixtures comprising ethanol/water and acetone/water (8:2 v/v). The resultant zein solutions are placed in a beaker and stirred with a magnetic stirrer.

In Example 6, the zein precipitates from solution after evaporation of the organic solvent until a zein concentration of 30% w/v is obtained. The product obtained in Example 6 did not have a pseudolatex formation, and large agglomerates/viscous lumps formed.

In Example 7, the organic solvent is evaporated over a period of 48 hours in a one liter beaker, and a zein concentration of 3% w/v is obtained. The pH range of the product was 5-7. The product of Example 7 did have pseudolatex formation. However, in addition to small nanoparticles, some larger lumps and agglomerates were formed.

The results indicate that the precipitation method is superior to the evaporation method. Table 2 below is a comparison of results obtained by these two methods.

TABLE 2

| Comparison of Results Obtained by Evaporation and Precipitation Methods | | | | |
|---|---|---|---|---|
| | Evaporation | | Precipitation | |
| Zein conc. (% w/v) | 30 | 3 | 6 | 3 |
| Pseudolatex formation (Y/N) | N | Y* | Y | Y |

*Dispersion agglomerated

EXAMPLES 8-9

Redispersibility of Zein Particles

In Examples 8-9, zein latexes prepared according to Example 4 are spray-dried using a Buchi Mini Spray dryer (Model 190, Brinkmann Instruments, Inc., Westbury, N.Y.; inlet temperature=90° C.). In Example 8, a 5% w/v zein solution was prepared in acetone/water (7/3 v/v). In Example 9, a 10% w/v zein solution was prepared in ethanol/water (6/4 v/v).

In each of Examples 8 and 9, fine zein particles smaller than about 10 $\mu$m are obtained. Most of the zein particles are smaller than about 5 $\mu$m.

EXAMPLE 10

Effect of pH Changes

In Examples 10a-d, zein pseudolatexes are prepared according to Example 4. A solvent mixture of ethanol and water (6/4) is prepared, and 6% zein w/v is added. 20 ml of the mixture is then 20 added to an external aqueous phase.

In Example 10a, the external aqueous phase comprises a 20 ml buffer solution prepared according to USP at different pH. The different buffer solutions and results are set forth in Table 3. From these results, it is concluded that a dispersion of zein can be formed in buffers of high pH.

TABLE 3

| Stirring time | pH 1.1 | pH 3 | pH 5 | pH 7.4 | pH 9 | pH 10 |
|---|---|---|---|---|---|---|
| 0 | large aggregates | | aggregates | | pseudolatex & little aggregates | |

TABLE 3-continued

| Stirring time | pH 1.1 | pH 3 | pH 5 | pH 7.4 | pH 9 | pH 10 |
|---|---|---|---|---|---|---|
| overnight | large aggregates | | aggregates | | pseudolatex & little aggregates | | pH 1.1: 0.1M HCl
pH 3: 0.2M potassium hydrogen phthalate and 0.2M HCl
pH 5: 0.2M potassium biphthalate and 0.2M NaOH
pH 7.4: 0.2M monobasic potassium phosphate and 0.2M NaOH
pH 9 and pH 10: 0.2M boric acid + potassium chloride and 0.2M NaOH In Example 10b, the external aqueous phase comprises a 20 ml buffer solution prepared according to USP of 0.1M citric acid and 0.2M Na₂HPO₄ at pH 3.5, pH 5, and pH 7.4. At each pH, large aggregates form when the zein solution is added.

In Example 10c, the external aqueous phase comprises a 20 ml solution with a pH 7.4 buffer with different ionic strengths using NaCl to adjust ionic strength to 0.144, 0.25, 0.5, 0.75 and 1.0. At each of these ionic strengths, large aggregates form when the zein solution is added. It is therefore concluded that ionic strength does not affect the formation of zein pseudolatexes.

In Example 10d, the external aqueous phase comprises a 20 ml solution with a pH 9.5 buffer made from ammonium carbonate-ammonia. An acceptable pseudolatex is produced after stirring overnight.

EXAMPLE 11

Zein Film Coatings

In Example 11, a zein pseudolatex is prepared according to the procedure set forth in Example 4. The solid content of the latex is 5% zein (w/v). The zein pseudolatex is then plasticized by adding 20% propylene glycol, based on the zein content. Thereafter, the zein latex is applied as a coating onto substrates.

In Example 11a, Nu-pareil beads are loaded with chlorpheniramine maleate, and thereafter coated with the zein latex in a Uni-Glatt fluidized bed coater equipped with a Wurster column. An inlet temperature of 60° C. is used. An approximate 10% weight gain is applied to the beads. The pseudolatex is found to be easy to use and does not contain any undispersed zein. No sticking or congealing is noted. The spray characteristics of the zein pseudolatex is similar to that of HPMC.

While the zein pseudolatex as prepared above was useful as a coating, it did not provide a slow release of the chlorpheniramine maleate from the zein coated beads (the drug was released at the same rate as the uncoated beads). Examination using scanning electron microscopy revealed numerous cracks in the film coat.

In Example 11b, DSC analysis was performed on the zein latex film samples that were cast at room temperature and at 60° C. The Tg of the room temperature sample was 327° K. and the Tg of the 60° C. film sample was 370° K., indicating that the film formed at the lower temperature was plasticized to a greater degree, possibly due to residual moisture in the film and the loss of the propylene glycol at 60° C.

In Example 11c, a second batch of zein latex (5% solid) is used to coat chlorpheniramine maleate-loaded beads under different operating conditions, with an inlet temperature of 35° C. The results of Example 11c were similar to those of Examples 11a and 11b, with scanning electron microscopy revealing numerous cracks in the coating.

In Example 11d, further studies are conducted to determine the effect of increasing amounts of plasticizer in the aqueous zein dispersion, and to determine the effect of relative humidity. A zein film containing equal amounts of propylene glycol and zein on a weight basis is determined to be flexible at about 0% relative humidity, but becomes very sticky at 50% relative humidity. For a zein film containing 35% propylene glycol on a weight basis of zein, at 50% relative humidity the film remains flexible. At higher relative humidities, the film becomes more sticky, and at lower relative humidities it slowly becomes more brittle as the film dried and moisture is lost from the film. From these studies, it is concluded that a propylene glycol range of about 10–40% would be suitable, with a propylene glycol range of 20–25% being most preferred.

EXAMPLE 12

Preparation of Zein Films

In Example 12, zein solutions are prepared with and without plasticizer, and cast into aluminum petri dishes and dried at room temperature. In each of Examples 12a–12, the zein is added to 5–7 ml of a solvent mixture of ethanol/water (Examples 12a and 12b) or acetone/water (Examples 12c and 12d) in a ratio of 8:2 v/v. In Examples 12a and 12c, the resultant solution comprises 20% zein w/v; in Examples 12b and 12d the resultant solution comprises 30% zein w/v. Propylene glycol 20–40% is incorporated into the solutions as a plasticizer prior to casting. Smooth, transparent, flexible films are formed from 25% or 30% w/v zein solutions in ethanol or acetone/water mixtures (8:2 v/v). However, the films became brittle after a few days and after storage of the films in a desiccator, possibly due to further water evaporation or evaporation of the propylene glycol. In order to improve the flexibility of the film, different plasticizers are added to the polymer solution. The results indicate that water-soluble plasticizers, e.g., glycerin, propylene glycol, and PEG 400, provide flexible films when compared to the water-insoluble plasticizers, e.g., dibutyl sebacate (DBS), triethyl citrate (TEC), tributyl citrate (TBC), acetyltributyl citrate (ATBC), and acetyltriethyl citrate (ATEC). Propylene glycol at a concentration from about 20 to about 25%, based on the amount of zein, appears to be the best plasticizer of those studied.

The examples provided above are not meant to be exclusive. Many other variations of the present invention would be obvious to those skilled in the art, and are contemplated to be within the scope of the appended claims.

What is claimed is:

1. A method for preparing an aqueous dispersion of zein, comprising
    preparing a solvent mixture comprising water and from about 60 to about 90 percent of an organic solvent selected from the group consisting of ethanol, acetone, and mixtures thereof,
    adding a material consisting essentially of zein to said solvent mixture in such a proportion to said solvent mixture that the zein dissolves in the solvent mixture,
    precipitating the zein by pouring said solution of zein as a stream into an aqueous phase under continuous mixing such that the zein precipitates as fine particles in a colloidal dispersion, and removing the organic solvent to obtain an aqueous dispersion comprising from about 0.1 to about 10 percent w/v of zein.

2. The method of claim 1, wherein said solvent mixture comprises ethanol:water in a ratio of about 8:2 v/v.

3. The method of claim 1, wherein said solvent mixture comprises ethanol:water in a ratio of about 6:4 v/v.

4. The method of claim 1, wherein said solvent mixture comprises acetone:water in a ratio of about 8:2 v/v.

5. The method of claim 1, wherein said solvent mixture comprises acetone:water in a ratio of about 6:4 v/v.

6. The method of claim 1, wherein the pH of the resulting aqueous zein dispersion is from about 4 to about 6.

7. The method of claim 1, further comprising adding an effective amount of a plasticizer to said aqueous dispersion of zein to provide a flexible film when said aqueous dispersion is applied to a substrate.

8. The method of claim 1, further comprising adding a solubilizing agent to said aqueous dispersion of zein.

9. The method of claim 1, further comprising adding a suitable buffer system to adjust the pH of said aqueous dispersion of zein to above about pH 9.

10. The zein powder produced by the method of claim 9.

11. The method of claim 1, further comprising adding an ammonium carbonate-ammonia buffer to said aqueous dispersion of zein to adjust the pH to above about pH 9.

12. A method for preparing a redispersible zein powder, comprising
preparing a solvent mixture comprising water and from about 60 to about 90 percent of an organic solvent selected from the group consisting of ethanol, acetone, and mixtures thereof,
adding a material consisting essentially of zein to said solvent mixture in such a proportion to said solvent mixture that the zein dissolves in the solvent mixture,
precipitating the zein by pouring said solution of zein as a stream into an aqueous phase under continuous mixing such that the zein precipitates as fine particles in a colloidal dispersion and removing the organic solvent to obtain an aqueous dispersion comprising from about 0.1 to about 10 percent w/v of zein, and
drying the resultant aqueous dispersion to obtain a zein powder which is redispersible in aqueous solutions.

13. The method of claim 12, wherein said aqueous dispersion is spray-dried to obtain a redispersible zein powder having a particle size ranging from about 0.1 to about 10 $\mu$m.

14. The method of claim 13, further comprising redispersing the zein powder in an aqueous solution prior to use in a coating process.

15. The zein powder produced by the method of claim 12.

16. A zein powder having a particle size ranging from about 0.1 to about 10 $\mu$m which is redispersible in an aqueous solution to provide an aqueous dispersion of zein wherein said zein is obtained by the process of claim 12.

17. An aqueous dispersion of zein produced by adding a material consisting essentially of zein to a solvent mixture comprising water and from about 60 to about 90 percent of an organic solvent selected from the group consisting of ethanol, acetone, and mixtures thereof, in such a proportion that the zein dissolves in the solvent mixture, and pouring said solution of zein as a stream into an aqueous phase under continuous mixing such that the zein precipitates as fine particles in a colloidal dispersion, the organic solvent thereafter being removed to obtain an aqueous dispersion comprising from about 0.1 to about 10 percent w/v of zein.

18. The aqueous dispersion of claim 17 comprising zein and a buffer in an amount effective to adjust the pH of the aqueous dispersion to above about pH 9.

19. The aqueous dispersion of claim 18, wherein said buffer is selected from the group consisting of an ammonium carbonate-ammonia buffer, a citric acid-sodium phosphate buffer, and a boric acid-potassium chloride-sodium hydroxide buffer.

20. The aqueous dispersion of claim 17, which has a pH from about 3 to about 7.

21. The aqueous disperion of claim 17, which comprises from about 5 to about 10 percent zein w/v, and having a pH from about 4 to about 6.

22. The aqueous dispersion of claim 17, wherein the particle size of the zein in said aqueous dispersion is from about 0.01 to about 2.0 $\mu$m.

23. The aqueous dispersion of claim 17, wherein the average particle size of the zein in said aqueous dispersion is from about 100 to about 300 nanometers.

24. The aqueous dispersion of claim 17, wherein the pH of the aqueous dispersion is from about 4.5 to about 5.5.

* * * * *